US00PP16495P3

(12) United States Plant Patent
McGranahan et al.

(10) Patent No.: US PP16,495 P3
(45) Date of Patent: May 2, 2006

(54) WALNUT TREE NAMED 'FORDE'

(50) Latin Name: *Juglans regia*
Varietal Denomination: Forde

(75) Inventors: Gale McGranahan, Davis, CA (US); Charles Leslie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 79 days.

(21) Appl. No.: 10/944,092

(22) Filed: Sep. 17, 2004

(65) Prior Publication Data

US 2006/0031973 P1 Feb. 9, 2006

Related U.S. Application Data

(63) Continuation-in-part of application No. 10/913,249, filed on Aug. 6, 2004, now abandoned.

(51) Int. Cl.
*A01H 5/00* (2006.01)

(52) U.S. Cl. ..... Plt./154

(58) Field of Classification Search ..... Plt./154
See application file for complete search history.

*Primary Examiner*—Anne Marie Grunberg
*Assistant Examiner*—June Hwu
(74) *Attorney, Agent, or Firm*—Morrison & Foerster LLP

(57) ABSTRACT

A new and distinct variety of walnut tree denominated 'Forde' is described. This new cultivar comes into bearing young, produces well mid-season, and bears a jumbo sized nut with a strong yet easily removed shell. The new tree also shows low susceptibility to walnut blight.

7 Drawing Sheets

FIELD OF THE INVENTION

Botanical/commercial classification: (*Juglans regia*)/new English walnut variety. Varietal denomination: cv. Forde.

BACKGROUND OF THE INVENTION

The present invention relates to a new and distinct variety of walnut tree *Juglans regia* which has been denominated varietally as 'Forde,' and more particularly to such a walnut tree which has a harvest date three to eight days earlier than the walnut tree variety 'Chandler' (U.S. Plant Pat. No. 4,388) and which further produces a walnut that is jumbo in size with light colored kernels and which can be processed in shell or cracked.

It has long been recognized as desirable to provide walnut trees bearing large crops which are ripe for commercial harvesting and shipment midseason and exhibit low susceptibility to walnut blight. The tree of the present variety, 'Forde,' produces a nut which is similar in some respects to common walnut tree varieties such as 'Chandler,' (U.S. Plant Pat. No. 4,388). However, the new variety is ready for harvest up to eight days before 'Chandler,' and ten days after the common reference cultivar 'Payne' (unpatented).

The new *Juglans regia* walnut tree of the present invention was created at Davis, Calif. in 1995 by a controlled cross of the cultivars 'Chico' and 'UC 61-25,' also known as 'Lara' (not patented). 'Forde' differs from 'Chico' in having larger nuts which are easier to remove from the shell, a later harvest and a more vigorous tree. 'Forde' differs from 'UC61-25' in having much lighter kernel color, a smoother shell, and unlike 'UC61-25', 'Forde' is protogynous. The pedigree is illustrated (FIG. 1).

Seeds from the cross were planted and the resulting 40 trees were carefully observed along with other trees in the walnut breeding program. When they began to bear nuts, data were collected annually on leafing date, first peak and last female flower bloom, first, peak and last male bloom, blight severity and yield (Table 1). Nuts were sampled, cracked, and data was collected on shell appearance, shell thickness, shell integrity, shell strength, nut weight, kernel weight, percent kernel, ease of kernel removal, kernel color, and percent kernel shrivel (Table 2). A single tree was selected from among progeny of this controlled cross based on its superior attributes. This selection was originally designated 'UC95-26-37,' and is now designated 'Forde' after Harold Forde, a University of California walnut breeder from 1948 to 1978.

The new cultivar 'Forde' was originally asexually reproduced by grafting in Davis, Calif., Parlier, Calif., and Chico, Calif. The new cultivar of the present invention has been propagated by grafting at Davis, Calif. on 'Paradox' hybrid rootstock. The distinctive characteristics of the new cultivar have been found to be stable and are transmitted to the new trees when asexually propagated. 'Forde' is stable and reproduces true to type.

SUMMARY OF THE INVENTION

It was found that the new cultivar exhibits the following combination of characteristics:

a) Comes into bearing young, with a good yield for a young tree at age 3;

b) Forms jumbo-sized walnuts with little size variation in a given harvest which possess strong well-filled shells and easy to remove light-colored kernels;

c) Can be processed inshell or cracked;

d) Bears fruit laterally;

e) Yields a walnut crop that can be harvested mid-season and prior to 'Chandler' (U.S. Plant Pat. No. 4,388);

f) Is protogynous (pollen sheds after female bloom occurs); and g) exhibits low susceptibility to walnut blight.

BRIEF DESCRIPTION OF THE TABLES

Table 1 shows comparative tree evaluations.

Table 2 shows nut and kernel traits.

BOTANICAL DESCRIPTION OF THE PLANT

The description is based on an ungrafted walnut on its own roots and trees propagated by grafting on Paradox rootstock and growing in an orchard at Davis, Calif. Data was collected on the own rooted tree from 1999, age 3 years, to 2003, age 7 years. In 2001, scionwood from this tree was collected and grafted onto Paradox rootstock for further evaluation in three sites: Davis, Chico and Kearney.

The Munsell Book of Color is used in the identification of color. Also, common color terms are to be accorded their ordinary dictionary significance.

Botanical classification: *Juglans regia.*

*Female parent.*—UC61-25 ('Lara') (unpatented).

*Male parent.*—'Chico' (unpatented).

Figure 1:
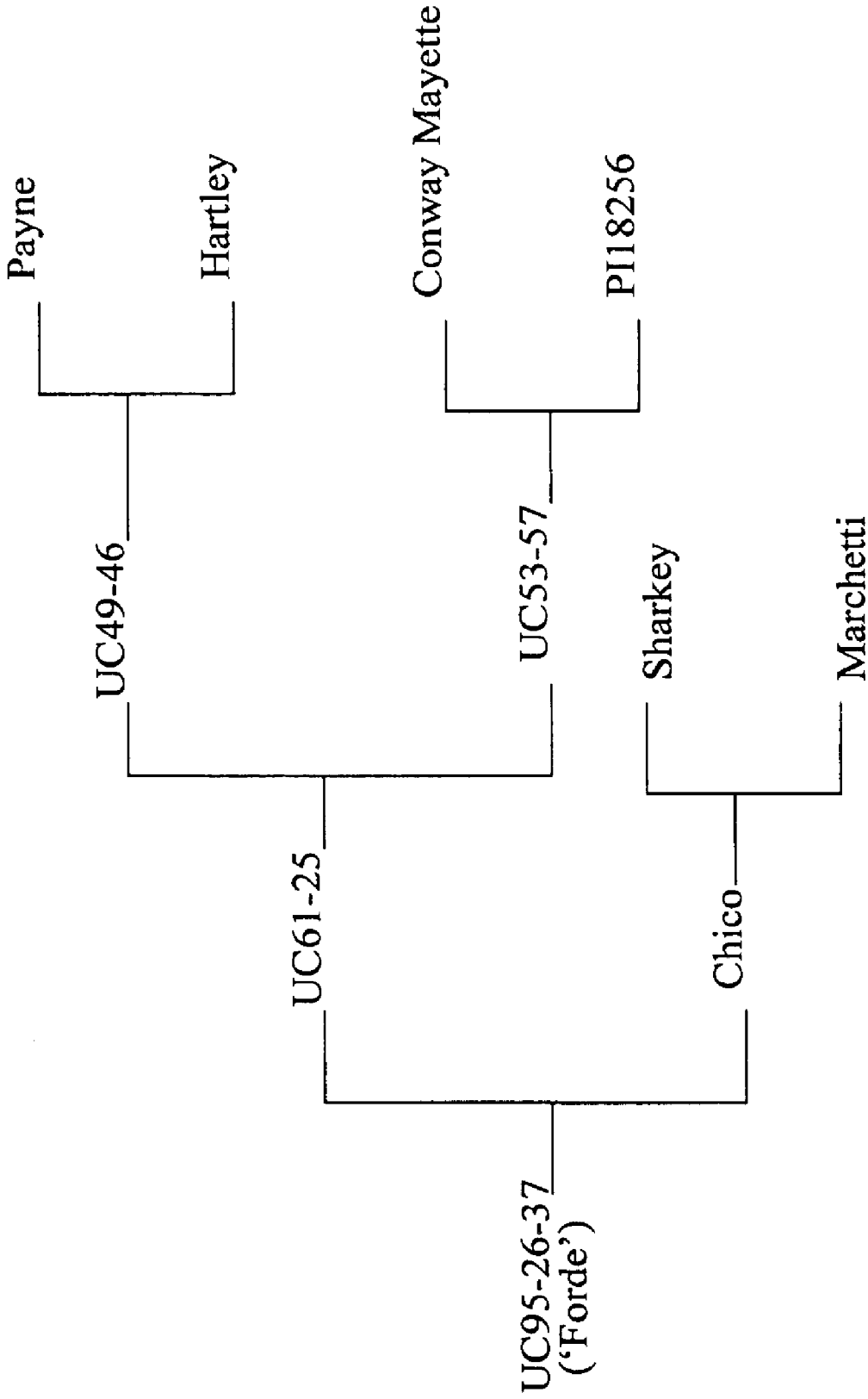
FIG. 1—shows the pedigree of the 'Forde' walnut.
Figure 2:
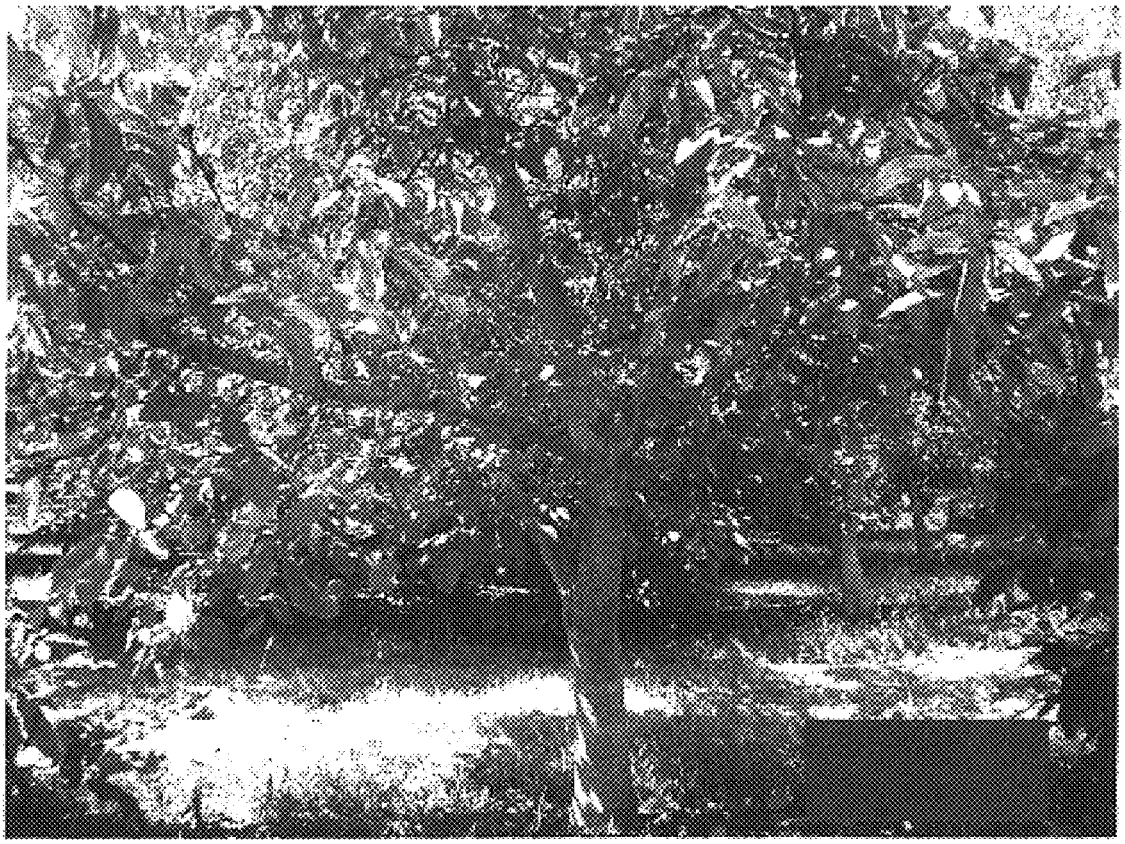
FIG. 2—shows a tree of the 'Forde' walnut at seven years.

The pedigree is shown (FIG. 1). The growth habit of the tree is illustrated in FIG. 2.

Figure 3:
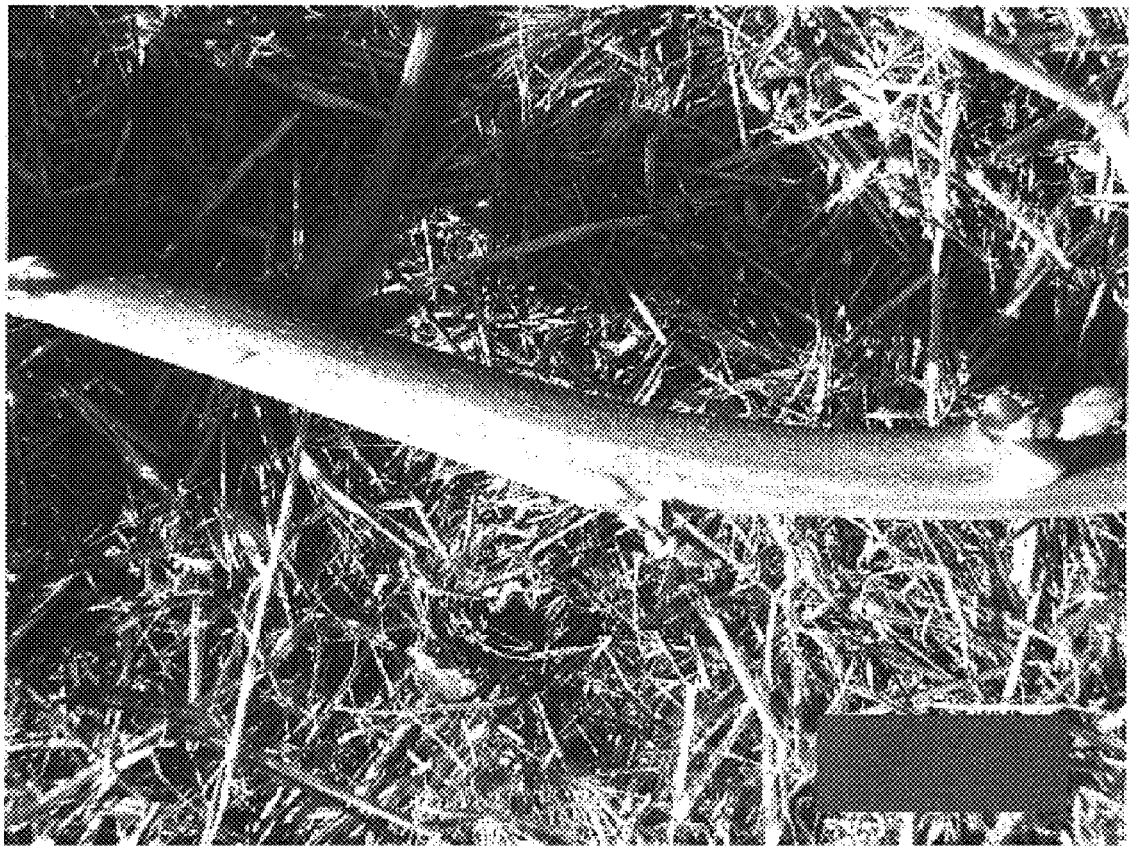
FIG. 3—shows a near view of the typical current season's stem of the 'Forde' walnut.
Figure 5:
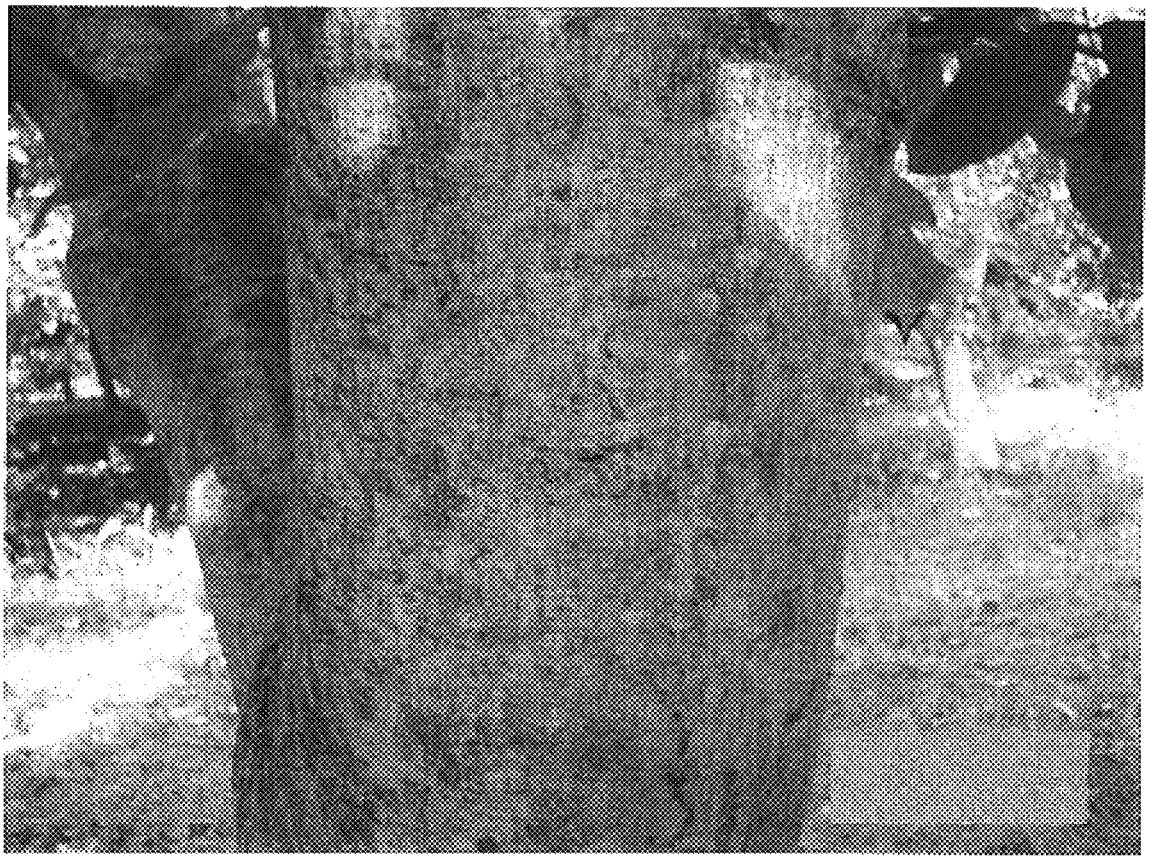
FIG. 5—shows a near view of the bark of the 'Forde' walnut.
Figure 6:
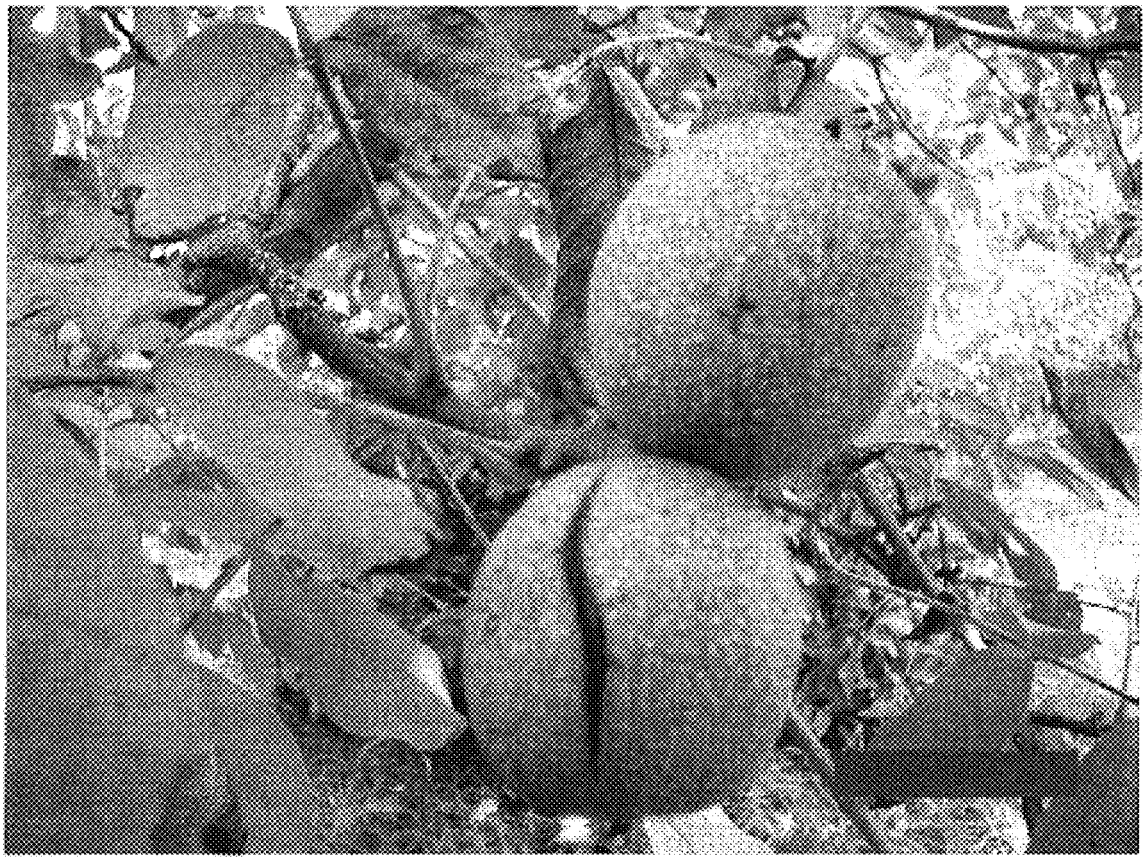
FIG. 6—shows nuts in the hull of the 'Forde' walnut.
Figure 7:
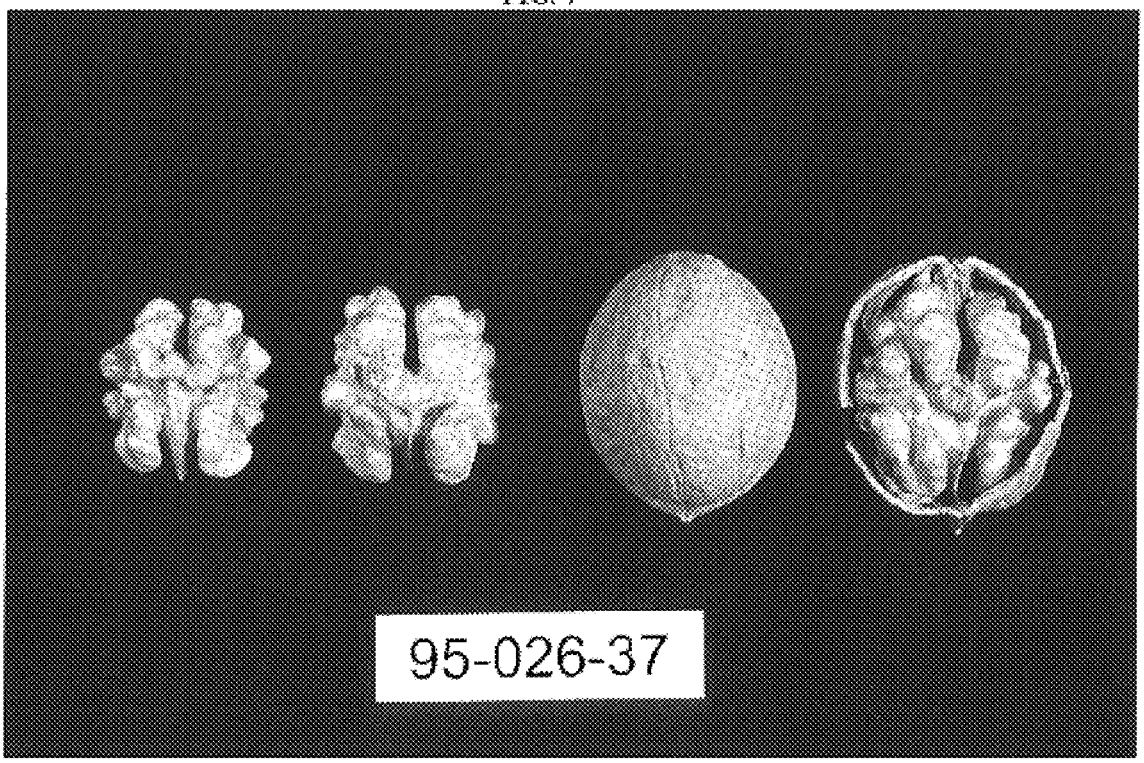
FIG. 7—shows kernels of the 'Forde' walnut.

Plant: The growth habit of the tree is illustrated in FIG. 2. This 7 year old tree was approximately 18 feet in height with a canopy diameter of approximately 5.3 meters. The trunk diameter at 30 cm above the ground is approximately 24 cm. The bark (as illustrated) is typical of *Juglans regia.* The young bark is brown (8.0YR 3.0/5.4) with numerous raised lenticels (FIG. 3). 'Forde''s lenticels are oval, measure 2–10 mm by 1–2 mm and are light brown grey 7.0YR 5.4/1.2 in Munsell's Book of Color. 'Forde''s bark color is grey-yellow (4.4Y 7.2, 3.8) with lighter brown-grey striations (7.0YR 5.4/1.2) (FIG. 5). On one to two year old bark there are about 43 lenticels per 2.5 cm of stem measuring approximately 1.5 cm in diameter. The surface texture of the trunk, branch, leaflets, hull and kernel is smooth. 'Forde' has moderate vigor, similar to 'Chandler'.

Figure 4:
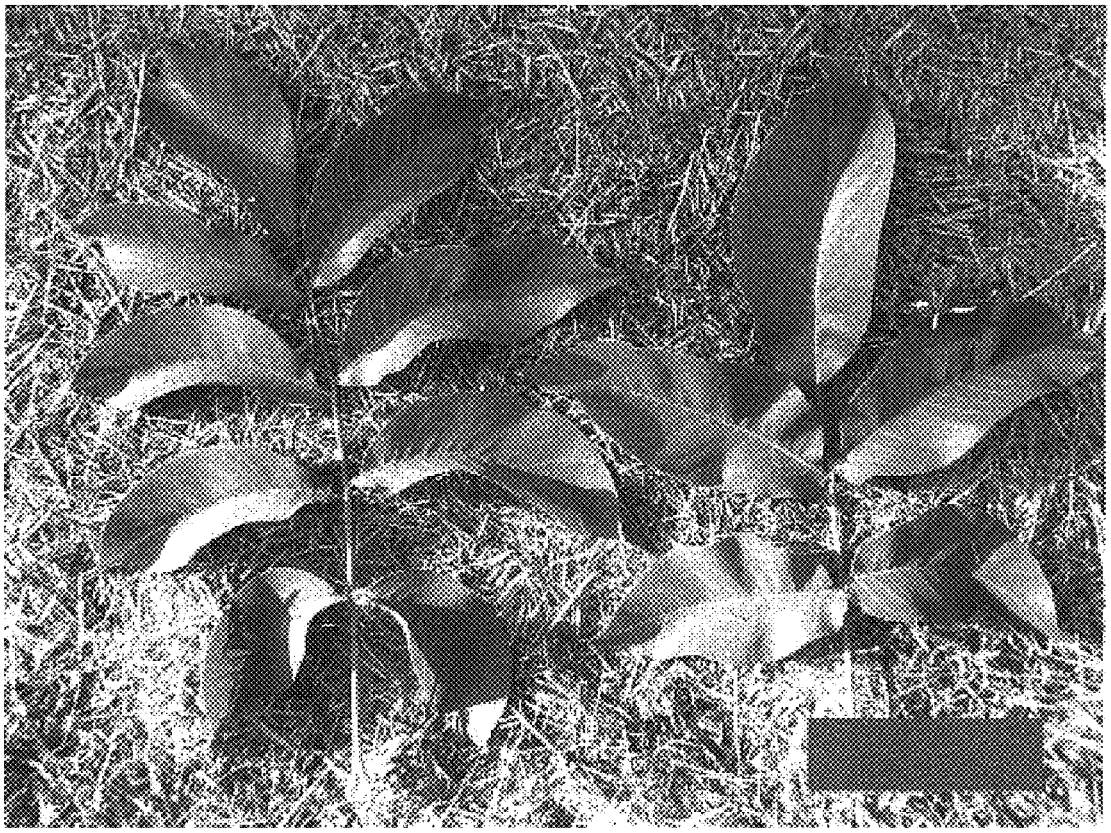
FIG. 4—shows a near view of the leaves of the 'Forde' walnut.

Foliage: The dark green foliage is illustrated (FIG. 4) and is typical of *Juglans regia.* Leaf out during 1999–2003 has occurred on April 1 on the average. For comparative purposes the 'Payne' cultivar leafed out 12 days earlier and the 'Chandler' cultivar leafed out 5 days later during the same years. The typical leaf coloration is moderate olive green, 8.2GY 3.2/6.1, on the upper surface and slightly lighter (5.3GY 5.2/9.7) on the lower surface. The leaves are pinnately compound with 5–7 leaflets. The full leaf length is approximately 40.3 cm and the width 29.9 cm. The terminal leaflet averages 15.1 cm in length and 6.3 cm in width. The middle leaflets average 14.9 cm in length and 5.1 cm in width and the proximal leaflets average 13.7 cm in length and 5.2 cm in width. If 7 leaflets are present the first (proximal) set is smallest averaging 10.1 cm in length and 4.6 cm in width. The leaflets are broadly elliptical and entire. The petiole averages 25.7 cm in length and is 1–2 mm in diameter. The entire rachis including the petiole measures 25.7 cm in length, 2–4 mm in diameter and the distance to the first leaflet (petiole) is 7 cm. The color is yellow-green 5GY 6/8.

Inflorescence: The tree is relatively precocious; a good yield being noted for a 3-year-old tree. Male flowers (catkins) were not present until age 5. This delay in male maturity is typical of *Juglans regia*. The catkin's diameter is about 15 mm and yellow-green (5GY 6/8). Catkin length ranges between 7 and 13 cm. From 1999 to 2003, the first female bloom occurred on average on April 7, peak bloom on April 12 and last bloom on April 18. From 1999 to 2003, average male flowering (pollen shedding) began April 15, peaked on April 20 and terminated April 26. In this protogynous tree, pollen shedding covers 15% of the pistillate bloom. A pollenizer would be needed for maximum yield in isolated areas. Both 'Vina' (not patented) and 'UC90-31-10' (patent applied for, application Ser. No. 10/943,371) would be satisfactory pollenizers. The female flowers are typical of *Juglans regia* with two flowers per inflorescence borne at both terminal and lateral positions on current season's growth. Approximately 100% of the lateral buds contain inflorescences making yields much greater than trees that only bear flowers terminally. A typical female flower is approximately 5 to 7 mm at anthesis and the floral organs are typical of *J. regia.* The flower fragrance is typical of *J. regia* and is not noticeably different than the foliage fragrance. At antithesis the flower itself appears vase shaped with two plumose curved stigmatic arms. The flowers measure 5–7 mm in length and 3–5 mm in diameter and are yellow-green (5GY 6/8) in color. They are borne usually in twos on a 1 cm spike.

Walnuts: The new cultivar harvests on average 3 days before 'Chandler' and three weeks after 'Payne' but is becoming earlier as the clone ages. In 2003, this new cultivar was ready for harvest on October 3, 7 days before 'Chandler' and 12 days after 'Payne.' Earlier leafing and harvest dates are typical for walnuts as a clone ages. The new cultivar has excellent yields of jumbo-sized walnuts. The hull is globose, moderate yellow-green (5GY 5/6), measures 4.7 cm long and 4.1–4.5 mm wide and is 5 mm thick. The oval nutshell is light tan, and measures 40.3 mm in length and 37.3 mm in width. The shell is strong and well sealed and the kernel is easy to remove. The kernel weighs 9.2 g and makes up 53.4% of the total nut weight of 17.2 g. Kernel color is considered excellent and scores mostly in the light to extra light categories of the USDA Standards for Grades of Shelled Walnuts as determined by using the standard Walnut Color Chart for kernels published by te Drieds Fruit Association of California. In addition kernels of Forde scored 54.6 on the Relative Light Index used by Diamond Walnut of Stockton, Calif. The kernels have a shiny surface comparable to that of the 'Chandler' walnut. These values are based on 5-year averages of ten walnut samples each year obtained from a young tree. The large plump kernels are approximately 33.6 mm in length and 31.6 mm in width. The kernel is essentially round and splits into halves easily. It is plump in comparison to 'Chandler'. It is typical of commercial walnuts in terms of flavor and firmness, the latter varying according to the percent moisture after drying.

Hardiness: The immature tree has withstood a temperature of 21° F. in 1998.

Chilling requirement: Trees have not exhibited staggered leafing and bloom, symptoms of lack of chilling since they have been under evaluation, however chilling accumulation (hours under 45° F.) has never been lower than 767 in 1999–2000.

Disease resistance and susceptibility: Susceptibility to walnut blight has been low. No other unusual resistance or susceptibility to insects and diseases has been observed to date.

Usage: The new cultivar of the present invention provides a walnut cultivar that harvests before 'Chandler' and has large light and extra light colored kernels that can be used cracked or in shell.

TABLE 1

TREE EVALUATIONS

| | Leafing date | DAP L | Male bloom date | DAP M | Female bloom date | DAP F | Harvest Date | DAP H |
|---|---|---|---|---|---|---|---|---|
| 1999 | | | | | | | | |
| Payne | 3/24 | 0 | 4/14 | 0 | 4/18 | 0 | 9/24 | 0 |
| Tulare | 4/10 | 17 | 4/17 | 3 | 4/25 | 7 | 10/5 | 11 |
| Chandler | 4/13 | 20 | 4/17 | 3 | 4/28 | 10 | 10/19 | 25 |
| Sexton | 4/6 | 13 | 4/18 | 4 | 4/19 | 1 | 10/1 | 7 |
| Gillet | 4/11 | 18 | | | 4/22 | 4 | 10/10 | 16 |
| Forde | 4/14 | 21 | | | 4/23 | 5 | 10/22 | 28 |
| 2000 | | | | | | | | |
| Payne | 3/19 | 0 | 3/31 | 0 | 4/5 | 0 | 9/13 | 0 |
| Tulare | 4/3 | 15 | 4/11 | 11 | 4/15 | 10 | 10/3 | 20 |
| Chandler | 4/4 | 16 | 4/12 | 12 | 4/20 | 15 | 10/12 | 29 |
| Sexton | 3/28 | 9 | 4/5 | 5 | 4/10 | 5 | 9/30 | 17 |
| Gillet | 3/30 | 11 | | | 4/7 | 2 | 9/28 | 13 |
| Forde | 4/3 | 15 | | | 4/10 | 5 | 10/7 | 24 |
| 2001 | | | | | | | | |
| Payne | 3/17 | 0 | 3/27 | 0 | 4/1 | 0 | 9/9 | 0 |
| Tulare | 3/29 | 12 | 4/10 | 13 | 4/20 | 20 | 9/27 | 15 |
| Chandler | 3/29 | 12 | 4/10 | 13 | 4/23 | 22 | 10/7 | 28 |
| Sexton | 3/22 | 5 | 3/26 | 0 | 4/7 | 6 | 9/29 | 20 |
| Gillet | 3/23 | 6 | 4/15 | 18 | 3/30 | −2 | 9/18 | 9 |
| Forde | 3/24 | 7 | 4/15 | 18 | 4/3 | 2 | 9/29 | 20 |
| 2002 | | | | | | | | |
| Payne | 3/27 | 0 | 4/6 | 0 | 4/12 | 0 | 9/18 | 0 |
| Tulare | 4/6 | 10 | 4/15 | 9 | 4/24 | 12 | 10/3 | 16 |
| Chandler | 4/7 | 11 | 4/17 | 11 | 4/27 | 15 | 10/9 | 21 |
| Sexton | 4/1 | 5 | 4/10 | 4 | 4/15 | 3 | 10/3 | 15 |
| Gillet | 4/1 | 5 | 4/23 | 17 | 4/11 | −1 | 10/4 | 16 |
| Forde | 4/2 | 6 | 4/23 | 17 | 4/13 | 1 | 10/6 | 18 |
| 2003 | | | | | | | | |
| Payne | 3/18 | 0 | 4/5 | 0 | 4/9 | 0 | 9/21 | 0 |
| Tulare | 4/5 | 18 | 4/18 | 13 | 4/26 | 17 | 10/5 | 14 |
| Chandler | 4/7 | 20 | 4/20 | 15 | 5/3 | 25 | 10/10 | 19 |
| Sexton | 3/24 | 6 | 4/5 | 0 | 4/9 | 0 | 10/6 | 15 |
| Gillet | 3/24 | 6 | 4/18 | 13 | 4/4 | −5 | 10/1 | 10 |
| Forde | 3/27 | 9 | 4/23 | 18 | 4/9 | 0 | 10/3 | 12 |
| 5 YEAR AVERAGE | | | | | | | | |
| Payne | 3/21 | 0 | 4/4 | 0 | 4/9 | 0 | 9/17 | 0 |
| Tulare | 4/4 | 14 | 4/14 | 10 | 4/22 | 13 | 10/3 | 17 |
| Chandler | 4/7 | 16 | 4/15 | 11 | 4/26 | 17 | 10/11 | 24 |
| Sexton | 3/29 | 8 | 4/6 | 2 | 4/12 | 3 | 10/1 | 15 |
| Gillet | 3/30 | 9 | 4/19 | 16 | 4/8 | 0 | 9/30 | 13 |
| Forde | 4/1 | 11 | 4/20 | 18 | 4/12 | 3 | 10/7 | 20 |

TABLE 1-continued

TREE EVALUATIONS

| | Season length | Overlap % | Male abundance | Female abundance | Lateral fruitfulness % | Yield | Blight |
|---|---|---|---|---|---|---|---|
| 1999 | | | | | | | |
| Payne | 159 | 89 | 6 | 7 | 100 | 6 | 3 |
| Tulare | 166 | 27 | 4 | 6 | 90 | 6 | 0 |
| Chandler | 174 | 53 | 4 | 5 | 90 | 5 | 3 |
| Sexton | 165 | 88 | 6 | 7 | 100 | 7 | 2 |
| Gillet | 171 | | | 5 | 90 | 5 | 0 |
| Forde | 182 | | | 6 | 100 | 4 | 0 |
| 2000 | | | | | | | |
| Payne | 161 | 89 | 6 | 6 | 100 | 6 | 5 |
| Tulare | 172 | 100 | 6 | 6 | 100 | 6 | 4 |
| Chandler | 175 | 67 | 4 | 5 | 90 | 4 | 0 |
| Sexton | 173 | 54 | 5 | 6 | 100 | 6 | 0 |
| Gillet | 172 | | | 6 | 100 | 6 | 0 |
| Forde | 180 | | | 5 | 100 | 6 | 0 |
| 2001 | | | | | | | |
| Payne | 161 | 89 | 7 | 6 | 100 | 5 | 8 |
| Tulare | 160 | 85 | 6 | 6 | 70 | 5 | 3 |
| Chandler | 167 | 38 | 5 | 5 | 100 | 4 | 2 |
| Sexton | 175 | 53 | 5 | 6 | 100 | 6 | 1 |
| Gillet | 172 | | 3 | 6 | 100 | 7 | 0 |
| Forde | 179 | | 2 | 6 | 100 | 7 | 0 |
| 2002 | | | | | | | |
| Payne | 159 | 60 | 7 | 6 | 100 | 7 | 3 |
| Tulare | 162 | 91 | 5 | 6 | 100 | 6 | 0 |
| Chandler | 165 | 75 | 5 | 6 | 100 | 6 | 1 |
| Sexton | 171 | 83 | 6 | 6 | 100 | 6 | 0 |
| Gillet | 176 | 40 | 4 | 6 | 100 | 6 | 0 |
| Forde | 176 | 11 | 4 | 6 | 100 | 6 | 0 |
| 2003 | | | | | | | |
| Payne | 165 | 62 | 5 | 6 | 100 | 6 | 7 |
| Tulare | 164 | 92 | 5 | 6 | 100 | 6 | 5 |
| Chandler | 160 | 50 | 4 | 6 | 100 | 4 | 0 |
| Sexton | 180 | 100 | 5 | 6 | 100 | 6 | 2 |
| Gillet | 180 | 42 | 6 | 6 | 100 | 7 | 1 |
| Forde | 177 | 20 | 4 | 6 | 100 | 7 | 2 |
| 5 YEAR AVERAGE | | | | | | | |
| Payne | 161 | 78 | 6.2 | 6.2 | 100 | 6 | 5.2 |
| Tulare | 165 | 79 | 5.2 | 6 | 92 | 5.8 | 2.4 |
| Chandler | 168 | 57 | 4.4 | 5.4 | 96 | 4.6 | 1.2 |
| Sexton | 173 | 76 | 5.4 | 6.2 | 100 | 6.2 | 1 |
| Gillet | 174 | 41 | 4.3 | 5.8 | 98 | 6.2 | 0.2 |
| Forde | 179 | 15 | 3.3 | 5.8 | 100 | 6 | 0.4 |

KEY TO TABLE 1

| | |
|---|---|
| Leafing date | Date when 50% of terminal buds have enlarged and the bud scales have split exposing the green leaves |
| DAP L | Days after Payne (reference cultivar) leafing |
| Male bloom date | Date when maximum pollen shedding occurs |
| DAP M | Days after Payne (reference cultivar) male bloom |
| Female bloom date | Date of maximum pistillate flower receptivity |
| DAP F | Days after Payne (reference cultivar) female bloom |
| Harvest Date | Date when 95% of the nuts separate from the hulls |
| DAP H | Days after Payne (reference cultivar) harvest |
| Season length | Days between female flowering and harvest |
| Overlap % | Percent of female bloom overlapped by male bloom |
| Male abundance | Male flower abundance: 3 low; 5 intermediate; 7 high |
| Female abundance | Female flower abundance: 3 low; 5 intermediate; 7 high |
| Lateral fruitfulness % | Percent of lateral buds with female flowers |
| Yield | Yield: 3 low; 5 intermediate; 7 high |
| Blight | Blight incidence: 3 low; 5 intermediate; 7 high |
| | DFA Dried Fruit Association of CA |

TABLE 2

NUT AND KERNEL TRAITS

| | SHELL | | | | | | |
|---|---|---|---|---|---|---|---|
| | Texture | Color | Seal | Strength | In-tegrity | Thick-ness | Packing tissue |
| **1999** | | | | | | | |
| Payne | 5 | 5 | 5 | 5 | 7 | 1.3 | 5 |
| Tulare | 5 | 6 | 4 | 4 | 7 | 1.2 | 5 |
| Chandler | 5 | 4 | 5 | 4 | 7 | 1.2 | 5 |
| Sexton | 5 | 5 | 6 | 6 | 7 | 1.5 | 5 |
| Gillet | 5 | 5 | 3 | 5 | 7 | 1.5 | 5 |
| Forde | 5 | 5 | 5 | 5 | 7 | 1.6 | 5 |
| **2000** | | | | | | | |
| Payne | 5 | 6 | 5 | 5 | 7 | 1.4 | 5 |
| Tulare | 6 | 6 | 4 | 5 | 7 | 1.3 | 5 |
| Chandler | 5 | 5 | 5 | 4 | 7 | 1.4 | 5 |
| Sexton | 4 | 6 | 5 | 6 | 7 | 1.7 | 5 |
| Gillet | 6 | 5 | 4 | 4 | 7 | 1.3 | 5 |
| Forde | 6 | 5 | 4 | 5 | 7 | 1.2 | 5 |
| **2001** | | | | | | | |
| Payne | 5 | 5 | 5 | 5 | 7 | 1.5 | 5 |
| Tulare | 6 | 6 | 5 | 4 | 7 | 1.3 | 5 |
| Chandler | 5 | 4 | 5 | 4 | 7 | 1.6 | 5 |
| Sexton | 4 | 5 | 5 | 5 | 7 | 1.6 | 5 |
| Gillet | 5 | 5 | 4 | 4 | 7 | 1.2 | 5 |
| Forde | 5 | 5 | 5 | 5 | 7 | 1.5 | 5 |
| **2002** | | | | | | | |
| Payne | 5 | 5 | 5 | 5 | 7 | 1.0 | 5 |
| Tulare | 5 | 5 | 5 | 4 | 7 | 1.2 | 5 |
| Chandler | 5 | 4 | 5 | 5 | 7 | 1.5 | 5 |
| Sexton | 4 | 5 | 5 | 5 | 7 | 1.4 | 5 |
| Gillet | 5 | 5 | 4 | 5 | 7 | 1.3 | 5 |
| Forde | 5 | 4 | 5 | 5 | 7 | 1.5 | 5 |
| **2003** | | | | | | | |
| Payne | 5 | 5 | 5 | 6 | 7 | 1.6 | 5 |
| Tulare | 5 | 6 | 5 | 4 | 7 | 1.2 | 5 |
| Chandler | 5 | 4 | 5 | 4 | 7 | 1.3 | 5 |
| Sexton | 4 | 5 | 5 | 5 | 7 | 1.5 | 5 |
| Gillet | 5 | 5 | 5 | 5 | 7 | 1.3 | 5 |
| Forde | 6 | 6 | 6 | 6 | 7 | 1.6 | 5 |
| **5 YEAR AVERAGE** | | | | | | | |
| Payne | 5 | 5 | 6 | 5.2 | 7 | 1.4 | 5 |
| Tulare | 5.2 | 5.6 | 4.6 | 4.2 | 7 | 1.2 | 5 |
| Chandler | 5 | 4.2 | 5 | 4.2 | 7 | 1.4 | 5 |
| Sexton | 4.2 | 5.2 | 5.2 | 5.4 | 7 | 1.5 | 5 |
| Gillet | 5.2 | 5 | 4 | 4.6 | 7 | 1.3 | 5 |
| Forde | 5.4 | 4.6 | 5 | 5.2 | 7 | 1.5 | 5 |

| | | | | KERNEL | | | |
|---|---|---|---|---|---|---|---|
| | Inshell weight | Kernel weight | Kernel % | Fill | Plump-ness | Ease of removal | Blanks % |
| **1999** | | | | | | | |
| Payne | 16.9 | 5.3 | 44.9 | 5 | 4 | 4 | 0 |
| Tulare | 14.0 | 7.7 | 57.7 | 5 | 5 | 4 | 0 |
| Chandler | 13.7 | 7.1 | 52.2 | 4 | 5 | 3 | 0 |
| Sexton | 14.2 | 6.9 | 48.4 | 5 | 5 | 4 | 0 |
| Gillet | 16.5 | 8.2 | 49.8 | 5 | 4 | 5 | 0 |
| Forde | 18.8 | 9.7 | 51.7 | 5 | 6 | 5 | 0 |

TABLE 2-continued

NUT AND KERNEL TRAITS

| | | | | | | | |
|---|---|---|---|---|---|---|---|
| **2000** | | | | | | | |
| Payne | 12.8 | 6.1 | 48.0 | 5 | 5 | 4 | 0 |
| Tulare | 16.4 | 9.2 | 56.5 | 5 | 5 | 5 | 0 |
| Chandler | 13.7 | 6.7 | 49.1 | 5 | 4 | 4 | 0 |
| Sexton | 17.0 | 6.6 | 50.7 | 6 | 5 | 5 | 0 |
| Gillet | 17.0 | 9.0 | 52.9 | 5 | 4 | 5 | 0 |
| Forde | 17.3 | 10.3 | 58.8 | 5 | 6 | 4 | 0 |
| **2001** | | | | | | | |
| Payne | 15.4 | 7.4 | 48.2 | 5 | 5 | 5 | 0 |
| Tulare | 16.9 | 8.8 | 52.5 | 5 | 5 | 5 | 0 |
| Chandler | 15.0 | 7.5 | 49.7 | 4 | 4 | 4 | 0 |
| Sexton | 18.0 | 8.2 | 51.2 | 6 | 5 | 5 | 0 |
| Gillet | 15.0 | 8.1 | 53.8 | 5 | 4 | 5 | 0 |
| Forde | 15.1 | 8.0 | 53.0 | 5 | 5 | 5 | 0 |
| **2002** | | | | | | | |
| Payne | 12.1 | 5.6 | 46.6 | 5 | 5 | 5 | 0 |
| Tulare | 15.0 | 8.2 | 55.0 | 5 | 5 | 5 | 0 |
| Chandler | 13.7 | 8.2 | 45.4 | 4 | 4 | 4 | 0 |
| Sexton | 16.5 | 9.9 | 53.4 | 6 | 5 | 5 | 0 |
| Gillet | 15.2 | 7.7 | 50.6 | 5 | 6 | 5 | 0 |
| Forde | 16.7 | 8.9 | 53.4 | 5 | 5 | 4 | 0 |
| **2003** | | | | | | | |
| Payne | 15.6 | 7.4 | 47.1 | 5 | 5 | 5 | 0 |
| Tulare | 15.2 | 8.5 | 55.9 | 6 | 5 | 4 | 10 |
| Chandler | 13.6 | 7.1 | 51.1 | 5 | 4 | 4 | 0 |
| Sexton | 15.4 | 7.7 | 50.2 | 5 | 5 | 5 | 0 |
| Gillet | 16.2 | 8.2 | 50.5 | 5 | 5 | 5 | 0 |
| Forde | 17.6 | 9.1 | 51.7 | 6 | 6 | 4 | 0 |
| **5 YEAR AVERAGE** | | | | | | | |
| Payne | 14.6 | 6.4 | 47 | 5 | 4.8 | 4.8 | 0 |
| Tulare | 15.5 | 8.5 | 55.5 | 5.2 | 5 | 4.6 | 2 |
| Chandler | 14 | 6.9 | 49.5 | 4.4 | 4.2 | 3.8 | 0 |
| Sexton | 16.2 | 8.3 | 50.8 | 5.6 | 5 | 4.8 | 0 |
| Gillet | 16 | 8.2 | 51.6 | 5 | 4.4 | 5 | 0 |
| Forde | 17.1 | 9.2 | 53.7 | 5 | 5.4 | 4.4 | 0 |

| | KERNEL | | | | | | |
|---|---|---|---|---|---|---|---|
| | Extra light % | Light % | Light amber % | Amber % | Tip shrivel % | Other shrivel % | Veins % |
| **1999** | | | | | | | |
| Payne | 60 | 30 | 20 | 0 | 0 | 29 | 30 |
| Tulare | 0 | 100 | 0 | 0 | 0 | 0 | 0 |
| Chandler | 90 | 10 | 0 | 0 | 30 | 0 | 0 |
| Sexton | 100 | 0 | 0 | 0 | 20 | 0 | 0 |
| Gillet | 0 | 100 | 0 | 0 | 0 | 0 | 0 |
| Forde | 0 | 100 | 0 | 0 | 0 | 0 | 0 |
| **2000** | | | | | | | |
| Payne | 0 | 100 | 0 | 0 | 1 | 0 | 30 |
| Tulare | 0 | 100 | 0 | 0 | 1 | 0 | 0 |
| Chandler | 60 | 40 | 0 | 0 | 40 | 0 | 0 |
| Sexton | 0 | 60 | 20 | 0 | 10 | 0 | 10 |
| Gillet | 0 | 90 | 10 | 0 | 20 | 0 | 20 |
| Forde | 0 | 90 | 0 | 10 | 10 | 0 | 0 |

TABLE 2-continued

NUT AND KERNEL TRAITS

| | | | | | | | |
|---|---|---|---|---|---|---|---|
| 2001 | | | | | | | |
| Payne | 30 | 70 | 0 | 0 | 0 | 0 | 20 |
| Tulare | 0 | 100 | 0 | 0 | 20 | 0 | 0 |
| Chandler | 100 | 0 | 0 | 0 | 10 | 0 | 0 |
| Sexton | 40 | 60 | 0 | 0 | 10 | 0 | 10 |
| Gillet | 0 | 90 | 10 | 0 | 0 | 0 | 0 |
| Forde | 0 | 90 | 10 | 0 | 0 | 0 | 0 |
| 2002 | | | | | | | |
| Payne | 0 | 90 | 10 | 0 | 0 | 0 | 0 |
| Tulare | 0 | 100 | 0 | 0 | 0 | 0 | 0 |
| Chandler | 100 | 0 | 0 | 0 | 40 | 0 | 0 |
| Sexton | 50 | 50 | 0 | 0 | 0 | 0 | 0 |
| Gillet | 0 | 100 | 0 | 0 | 0 | 10 | 10 |
| Forde | 100 | 0 | 0 | 0 | 0 | 0 | 0 |
| 2003 | | | | | | | |
| Payne | 0 | 90 | 10 | 0 | 0 | 0 | 10 |
| Tulare | 33 | 67 | 0 | 0 | 0 | 0 | 0 |
| Chandler | 100 | 0 | 0 | 0 | 20 | 0 | 0 |
| Sexton | 40 | 40 | 20 | 0 | 20 | 20 | 0 |
| Gillet | 10 | 90 | 0 | 0 | 10 | 0 | 0 |
| Forde | 60 | 50 | 0 | 0 | 10 | 0 | 0 |
| 5 YEAR AVERAGE | | | | | | | |
| Payne | 18 | 76 | 6 | 0 | 0.2 | 4 | 16 |
| Tulare | 7 | 93 | 0 | 0 | 4 | 0 | 0 |
| Chandler | 90 | 10 | 0 | 0 | 26 | 0 | 0 |
| Sexton | 46 | 46 | 8 | 0 | 12 | 4 | 4 |

TABLE 2-continued

NUT AND KERNEL TRAITS

| | | | | | | | |
|---|---|---|---|---|---|---|---|
| Gillet | 2 | 94 | 4 | 0 | 6 | 2 | 6 |
| Forde | 30 | 56 | 2 | 2 | 4 | 0 | 0 |

KEY FOR TABLE 2

| | |
|---|---|
| Texture | Shell texture: 3 smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial area of shell missing; 5 small area of missing shell; 6 stem end hole; 7 complete shell |
| Thickness | Shell thickness at mid-cheek in mm |
| Packing tissue | Inner lining: 3 thin; 5 medium; 7 thick |
| Inshell weight | gm |
| Kernel weight | gm |
| Kernel % | Kernel wt/ inshell wt × 100 |
| Fill | Kernel fill: 3 poor; 5 moderate; 7 well |
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like Chandler |
| Other shrivel % | Percent of kernels with more substantial shrivel |
| Veins % | Percent of kernels with conspicuous veins |
| | DFA Dried Fruit Association of CA |

We claim:

1. A new and distinct variety of walnut tree substantially as shown and described herein.

* * * * *